US00RE45130E

(19) United States
(12) Reissued Patent
Figulla et al.

(10) Patent Number: US RE45,130 E
(45) Date of Reissued Patent: Sep. 9, 2014

(54) DEVICE FOR FASTENING AND ANCHORING CARDIAC VALVE PROSTHESES

(75) Inventors: Hans-Reiner Figulla, Jena (DE); Markus Ferrari, Jena (DE); Carsten Weber, Jena (DE); Thomas Peschel, Jena (DE); Christoph Damm, Jena (DE)

(73) Assignee: JenaValve Technology GmbH, Munich (DE)

(21) Appl. No.: 12/213,991

(22) Filed: Jun. 26, 2008

Related U.S. Patent Documents

Reissue of:
(64) Patent No.: 7,198,646
Issued: Apr. 3, 2007
Appl. No.: 10/204,990
PCT Filed: Feb. 28, 2001
PCT No.: PCT/DE01/00837
§ 371 (c)(1),
(2), (4) Date: Nov. 25, 2002
PCT Pub. No.: WO01/62189
PCT Pub. Date: Aug. 30, 2001

(30) Foreign Application Priority Data

Feb. 28, 2000 (DE) ..... 100 10 074

(51) Int. Cl.
*A61F 2/24* (2006.01)
*A61F 2/06* (2013.01)

(52) U.S. Cl.
USPC ..... 623/1.15; 623/900; 623/1.26; 623/2.18

(58) Field of Classification Search
USPC ..... 623/2.11–2.19, 1.24, 1.26, 900, 1.15
See application file for complete search history.

(56) References Cited

U.S. PATENT DOCUMENTS 3,755,823 A 9/1973 Hancock
4,106,129 A 8/1978 Carpentier et al.
RE30,912 E * 4/1982 Hancock ..... 623/2.1
4,922,905 A 5/1990 Strecker
4,994,077 A 2/1991 Dobben
5,002,566 A 3/1991 Carpentier et al.
5,061,277 A 10/1991 Carpentier et al.
5,094,661 A 3/1992 Levy et al.
5,104,407 A 4/1992 Lam et al.
5,163,953 A 11/1992 Vince (Continued)

FOREIGN PATENT DOCUMENTS

DE 19546692 A1 6/1997
DE 19633901 A1 * 2/1998 ..... A61F 2/04
DE 20003874 U1 6/2000
DE 19857887 A1 7/2000
DE 10010073 A1 9/2001

(Continued)

OTHER PUBLICATIONS

Aortenklappenbioprothese erfolgreich in der Entwicklung, (1 page) May 16, 2003.

(Continued)

*Primary Examiner* — Thomas J Sweet
*Assistant Examiner* — Cheryl Miller
(74) *Attorney, Agent, or Firm* — Bookoff McAndrews, PLLC

(57) ABSTRACT

This invention relates to a device for fastening and anchoring heart valve prostheses which is essentially formed of wire-shaped interconnected elements. The aim of the invention is to be able to be implant, in a minimally invasive manner, a device of this type via the aorta by compressing the device to make it smaller, and by extending the same at the site of implantation, whereby ensuring a secure retention and a secure sealing with regard to the aorta wall. To this end, the invention provides that for fastening and supporting a cardiac valve prosthesis, three identical pairs of arched elements are interconnected, with a configuration that is offset by 120°, by means of solid body articulations. These solid body articulations carry out the function of pivot bearings.

40 Claims, 1 Drawing Sheet

(56) References Cited

U.S. PATENT DOCUMENTS 5,197,979 A 3/1993 Quintero et al.
5,234,456 A * 8/1993 Silvestrini ..... 623/1.2
5,279,612 A 1/1994 Eberhardt
5,332,402 A 7/1994 Teitelbaum
5,336,258 A 8/1994 Quintero et al.
5,342,348 A * 8/1994 Kaplan ..... 604/891.1
5,352,240 A 10/1994 Ross
5,368,608 A 11/1994 Levy et al.
5,397,351 A * 3/1995 Pavcnik et al. ..... 623/2.35
5,411,552 A * 5/1995 Andersen et al. ..... 623/2.18
5,456,713 A 10/1995 Chuter
5,476,508 A * 12/1995 Amstrup ..... 623/1.2
5,509,930 A 4/1996 Love
5,549,666 A 8/1996 Hata et al.
5,595,571 A 1/1997 Jaffe et al.
5,613,982 A 3/1997 Goldstein
5,632,778 A 5/1997 Goldstein
5,674,298 A 10/1997 Levy et al.
5,679,112 A 10/1997 Levy et al.
5,683,451 A 11/1997 Lenker et al.
5,697,972 A 12/1997 Kim et al.
5,713,953 A 2/1998 Vallana et al.
5,746,775 A 5/1998 Levy et al.
5,755,777 A 5/1998 Chuter
5,824,041 A 10/1998 Lenker et al.
5,824,080 A 10/1998 Lamuraglia
5,840,081 A 11/1998 Andersen et al.
5,841,382 A 11/1998 Walden et al.
5,843,181 A 12/1998 Jaffe et al.
5,853,419 A * 12/1998 Imran ..... 623/1.15
5,855,601 A 1/1999 Bessler et al.
5,876,434 A 3/1999 Flomenblit et al.
5,880,242 A 3/1999 Hu et al.
5,899,936 A 5/1999 Goldstein
5,928,281 A 7/1999 Huynh et al.
5,935,163 A 8/1999 Gabbay
5,104,407 B1 9/1999 Lam et al.
5,964,798 A * 10/1999 Imran ..... 623/1.12
6,001,126 A 12/1999 Nguyen-Thien-Nhon
5,061,277 B1 2/2000 Carpentier et al.
6,077,297 A 6/2000 Robinson et al.
6,093,530 A 7/2000 McIlroy et al.
6,102,944 A 8/2000 Huynh et al.
6,117,169 A 9/2000 Moe
6,126,685 A 10/2000 Lenker et al.
6,146,417 A * 11/2000 Ischinger ..... 623/1.15
6,168,614 B1 1/2001 Andersen et al.
6,177,514 B1 1/2001 Pathak et al.
6,183,481 B1 2/2001 Lee et al.
6,190,405 B1 * 2/2001 Culombo et al. ..... 623/1.15
6,200,336 B1 3/2001 Pavcnik et al.
6,214,055 B1 4/2001 Simionescu et al.
6,231,602 B1 5/2001 Carpentier et al.
6,245,102 B1 * 6/2001 Jayaraman ..... 623/1.15
6,254,564 B1 7/2001 Wilk et al.
6,254,636 B1 7/2001 Peredo
6,283,995 B1 9/2001 Moe et al.
6,287,338 B1 9/2001 Sarnowski et al.
6,338,740 B1 1/2002 Carpentier
6,342,070 B1 1/2002 Nguyen-Thien-Nhon
6,344,044 B1 2/2002 Fulkerson et al.
6,350,278 B1 2/2002 Lenker et al.
6,379,740 B1 4/2002 Rinaldi et al.
6,391,538 B1 5/2002 Vyavahare et al.
6,425,916 B1 * 7/2002 Garrison et al. ..... 623/2.11
6,454,799 B1 9/2002 Schreck
6,471,723 B1 10/2002 Ashworth et al.
6,478,819 B2 11/2002 Moe
6,508,833 B2 1/2003 Pavcnik et al.
6,509,145 B1 1/2003 Torrianni
6,521,179 B1 2/2003 Girardot et al.
6,540,782 B1 4/2003 Snyders
6,558,417 B2 5/2003 Peredo
6,558,418 B2 5/2003 Carpentier et al.
6,572,642 B2 6/2003 Rinaldi et al.
6,582,462 B1 6/2003 Andersen et al.
6,585,766 B1 7/2003 Huynh et al.
6,613,086 B1 9/2003 Moe et al.
6,626,939 B1 * 9/2003 Burnside et al. ..... 623/1.38
6,682,559 B2 1/2004 Myers et al.
6,730,118 B2 5/2004 Spenser et al.
6,736,845 B2 5/2004 Marquez et al.
6,743,252 B1 * 6/2004 Bates et al. ..... 623/1.15
6,767,362 B2 7/2004 Schreck
6,773,455 B2 * 8/2004 Allen et al. ..... 623/1.15
6,790,230 B2 9/2004 Beyersdorf et al.
6,808,529 B2 10/2004 Fulkerson
6,821,211 B2 11/2004 Otten et al.
6,821,297 B2 11/2004 Snyders
6,824,970 B2 11/2004 Vyavahare et al.
6,830,584 B1 12/2004 Seguin
6,861,211 B2 3/2005 Levy et al.
6,872,226 B2 3/2005 Cali et al.
6,881,199 B2 4/2005 Wilk et al.
6,893,460 B2 5/2005 Spenser et al.
6,908,481 B2 6/2005 Cribier
6,911,043 B2 6/2005 Myers et al.
6,945,997 B2 9/2005 Huynh et al.
6,974,474 B2 12/2005 Pavcnik et al.
7,014,655 B2 3/2006 Barbarash et al.
7,018,406 B2 3/2006 Seguin et al.
7,037,333 B2 5/2006 Myers et al.
7,050,276 B2 5/2006 Nishiyama
7,078,163 B2 7/2006 Torrianni
7,081,132 B2 7/2006 Cook et al.
7,137,184 B2 11/2006 Schreck et al.
7,141,064 B2 11/2006 Scott et al.
7,163,556 B2 1/2007 Xie et al.
7,189,259 B2 3/2007 Simionescu et al.
7,198,646 B2 4/2007 Figulla et al.
7,201,772 B2 4/2007 Schwammenthal et al.
7,238,200 B2 7/2007 Lee et al.
7,252,682 B2 8/2007 Seguin
7,267,686 B2 * 9/2007 DiMatteo et al. ..... 623/1.24
7,318,278 B2 1/2008 Zhang et al.
7,318,998 B2 1/2008 Goldstein et al.
7,322,932 B2 1/2008 Xie et al.
7,329,278 B2 2/2008 Seguin et al.
7,381,218 B2 6/2008 Schreck
7,393,360 B2 7/2008 Spenser et al.
7,399,315 B2 7/2008 Iobbi
7,452,371 B2 11/2008 Pavcnik et al.
7,473,275 B2 1/2009 Marquez
7,704,222 B2 4/2010 Wilk et al.
7,736,327 B2 6/2010 Wilk et al.
2001/0011187 A1 8/2001 Pavcnik et al.
2001/0021872 A1 * 9/2001 Bailey et al. ..... 623/1.24
2001/0039450 A1 11/2001 Pavcnik et al.
2002/0032481 A1 3/2002 Gabbay
2002/0055775 A1 5/2002 Carpentier et al.
2002/0111668 A1 * 8/2002 Smith ..... 623/1.13
2002/0123790 A1 9/2002 White et al.
2002/0133226 A1 9/2002 Marquez et al.
2002/0198594 A1 12/2002 Schreck
2003/0027332 A1 2/2003 Lafrance et al.
2003/0036791 A1 2/2003 Philipp et al.
2003/0036795 A1 2/2003 Andersen et al.
2003/0040792 A1 2/2003 Gabbay
2003/0050694 A1 3/2003 Yang et al.
2003/0055495 A1 3/2003 Pease et al.
2003/0065386 A1 4/2003 Weadock
2003/0114913 A1 6/2003 Spenser et al.
2003/0125795 A1 7/2003 Pavcnik et al.
2003/0130726 A1 * 7/2003 Thorpe et al. ..... 623/1.24
2003/0139796 A1 7/2003 Sequin et al.
2003/0139803 A1 7/2003 Sequin et al.
2003/0149476 A1 8/2003 Damm et al.
2003/0153974 A1 8/2003 Spenser et al.
2003/0195620 A1 10/2003 Huynh et al.
2003/0236570 A1 12/2003 Cook et al.
2004/0006380 A1 1/2004 Buck et al.
2004/0039436 A1 2/2004 Spenser et al.
2004/0049262 A1 3/2004 Obermiller et al.
2004/0073289 A1 4/2004 Hartley et al.

(56) References Cited

U.S. PATENT DOCUMENTS

| | | | |
|---|---|---|---|
| 2004/0078950 | A1 | 4/2004 | Schreck et al. |
| 2004/0117004 | A1 | 6/2004 | Osborne et al. |
| 2004/0117009 | A1 | 6/2004 | Cali et al. |
| 2004/0148018 | A1 | 7/2004 | Carpentier et al. |
| 2004/0153145 | A1 | 8/2004 | Simionescu et al. |
| 2004/0186558 | A1 | 9/2004 | Pavcnik et al. |
| 2004/0186563 | A1 | 9/2004 | Lobbi |
| 2004/0186565 | A1 | 9/2004 | Schreck |
| 2004/0193244 | A1 | 9/2004 | Hartley et al. |
| 2004/0210301 | A1 | 10/2004 | Obermiller et al. |
| 2004/0210304 | A1 | 10/2004 | Seguin et al. |
| 2004/0260389 | A1 | 12/2004 | Case et al. |
| 2005/0009000 | A1 | 1/2005 | Wilhelm et al. |
| 2005/0033220 | A1 | 2/2005 | Wilk et al. |
| 2005/0033398 | A1 | 2/2005 | Seguin |
| 2005/0043790 | A1 | 2/2005 | Seguin |
| 2005/0049692 | A1 | 3/2005 | Numamoto et al. |
| 2005/0075725 | A1 | 4/2005 | Rowe |
| 2005/0075776 | A1 | 4/2005 | Cho |
| 2005/0096726 | A1 | 5/2005 | Sequin et al. |
| 2005/0096736 | A1 | 5/2005 | Osse et al. |
| 2005/0098547 | A1 | 5/2005 | Cali et al. |
| 2005/0113910 | A1 | 5/2005 | Paniagua et al. |
| 2005/0119728 | A1 | 6/2005 | Sarac |
| 2005/0119736 | A1 | 6/2005 | Zilla et al. |
| 2005/0137687 | A1 | 6/2005 | Salahieh et al. |
| 2005/0137688 | A1 | 6/2005 | Salahieh et al. |
| 2005/0137690 | A1 | 6/2005 | Salahieh et al. |
| 2005/0137697 | A1 | 6/2005 | Salahieh et al. |
| 2005/0137698 | A1 | 6/2005 | Salahieh et al. |
| 2005/0137702 | A1 | 6/2005 | Haug et al. |
| 2005/0143804 | A1 | 6/2005 | Haverkost |
| 2005/0143807 | A1 | 6/2005 | Pavcnik et al. |
| 2005/0149166 | A1 | 7/2005 | Schaeffer et al. |
| 2005/0150775 | A1 | 7/2005 | Zhang et al. |
| 2005/0171597 | A1 | 8/2005 | Boatman et al. |
| 2005/0171598 | A1 | 8/2005 | Schaeffer |
| 2005/0192665 | A1 | 9/2005 | Spenser et al. |
| 2005/0197695 | A1 | 9/2005 | Stacchino et al. |
| 2005/0222668 | A1 | 10/2005 | Schaeffer et al. |
| 2005/0234546 | A1 | 10/2005 | Nugent et al. |
| 2005/0267560 | A1 | 12/2005 | Bates |
| 2006/0009842 | A1 | 1/2006 | Huynh et al. |
| 2006/0025857 | A1 | 2/2006 | Bergheim et al. |
| 2006/0047343 | A1 | 3/2006 | Oviatt et al. |
| 2006/0058864 | A1 | 3/2006 | Schaeffer et al. |
| 2006/0074484 | A1 | 4/2006 | Huber |
| 2006/0111770 | A1 | 5/2006 | Pavcnik et al. |
| 2006/0142846 | A1 | 6/2006 | Pavcnik et al. |
| 2006/0149360 | A1 | 7/2006 | Schwammenthal et al. |
| 2006/0167543 | A1 | 7/2006 | Bailey et al. |
| 2006/0193885 | A1 | 8/2006 | Neethling et al. |
| 2006/0210597 | A1 | 9/2006 | Hiles |
| 2006/0229718 | A1 | 10/2006 | Marquez |
| 2006/0229719 | A1 | 10/2006 | Marquez et al. |
| 2006/0246584 | A1 | 11/2006 | Covelli |
| 2006/0259134 | A1 | 11/2006 | Schwammenthal et al. |
| 2006/0259136 | A1 | 11/2006 | Nguyen et al. |
| 2006/0265056 | A1 | 11/2006 | Nguyen et al. |
| 2006/0287717 | A1 | 12/2006 | Rowe et al. |
| 2006/0287719 | A1 | 12/2006 | Rowe et al. |
| 2006/0290027 | A1 | 12/2006 | O'Connor et al. |
| 2006/0293745 | A1 | 12/2006 | Carpentier et al. |
| 2007/0005129 | A1 | 1/2007 | Damm et al. |
| 2007/0005131 | A1 | 1/2007 | Taylor |
| 2007/0005132 | A1 | 1/2007 | Simionescu et al. |
| 2007/0020248 | A1 | 1/2007 | Everaerts et al. |
| 2007/0021826 | A1 | 1/2007 | Case et al. |
| 2007/0027535 | A1 | 2/2007 | Purdy, Jr. et al. |
| 2007/0038291 | A1 | 2/2007 | Case et al. |
| 2007/0038295 | A1 | 2/2007 | Case et al. |
| 2007/0043435 | A1 | 2/2007 | Seguin et al. |
| 2007/0050014 | A1 | 3/2007 | Johnson |
| 2007/0088431 | A1 | 4/2007 | Bourang et al. |
| 2007/0093887 | A1 | 4/2007 | Case et al. |
| 2007/0100435 | A1 | 5/2007 | Case et al. |
| 2007/0100440 | A1 | 5/2007 | Figulla et al. |
| 2007/0112422 | A1 | 5/2007 | Dehdashtian |
| 2007/0123700 | A1 | 5/2007 | Ueda et al. |
| 2007/0123979 | A1 | 5/2007 | Perier et al. |
| 2007/0142906 | A1 | 6/2007 | Figulla et al. |
| 2007/0162103 | A1 | 7/2007 | Case et al. |
| 2007/0173932 | A1 | 7/2007 | Cali et al. |
| 2007/0179592 | A1 | 8/2007 | Schaeffer |
| 2007/0185565 | A1 | 8/2007 | Schwammenthal et al. |
| 2007/0203576 | A1 | 8/2007 | Lee et al. |
| 2007/0213813 | A1 | 9/2007 | Von Segesser et al. |
| 2007/0239271 | A1 | 10/2007 | Nguyen |
| 2007/0244551 | A1 | 10/2007 | Stobie |
| 2007/0260327 | A1 | 11/2007 | Case et al. |
| 2007/0288087 | A1 | 12/2007 | Fearnot et al. |
| 2008/0004688 | A1 | 1/2008 | Spenser et al. |
| 2008/0021546 | A1 | 1/2008 | Patz et al. |
| 2008/0033534 | A1 | 2/2008 | Cook et al. |
| 2008/0065011 | A1 | 3/2008 | Marchand et al. |
| 2008/0071361 | A1 | 3/2008 | Tuval et al. |
| 2008/0071362 | A1 | 3/2008 | Tuval et al. |
| 2008/0071363 | A1 | 3/2008 | Tuval et al. |
| 2008/0071366 | A1 | 3/2008 | Tuval et al. |
| 2008/0071368 | A1 | 3/2008 | Tuval et al. |
| 2008/0071369 | A1 | 3/2008 | Tuval et al. |
| 2008/0077236 | A1 | 3/2008 | Letac et al. |
| 2008/0086205 | A1 | 4/2008 | Gordy et al. |
| 2008/0097586 | A1 | 4/2008 | Pavcnik et al. |
| 2008/0102439 | A1 | 5/2008 | Tian et al. |
| 2008/0133003 | A1 | 6/2008 | Seguin et al. |
| 2008/0140189 | A1 | 6/2008 | Nguyen et al. |
| 2008/0154355 | A1 | 6/2008 | Benichou et al. |
| 2008/0200977 | A1 | 8/2008 | Paul et al. |
| 2008/0215143 | A1 | 9/2008 | Seguin |
| 2008/0262602 | A1 | 10/2008 | Wilk et al. |
| 2008/0269878 | A1 | 10/2008 | Iobbi |
| 2008/0275549 | A1 | 11/2008 | Rowe |

FOREIGN PATENT DOCUMENTS

| | | | |
|---|---|---|---|
| DE | 10010074 | A1 | 10/2001 |
| DE | 101 21 210 | A1 | 11/2002 |
| DE | 19546692 | C2 | 11/2002 |
| DE | 10010074 | B4 | 4/2005 |
| DE | 19857887 | B4 | 5/2005 |
| DE | 10010073 | B4 | 12/2005 |
| EP | 0084395 | A1 | 7/1983 |
| EP | 0458877 | A0 | 8/1990 |
| EP | 0402036 | B1 | 12/1990 |
| EP | 0402176 | B1 | 12/1990 |
| EP | 0458877 | B1 | 4/1991 |
| EP | 0515324 | A1 | 11/1992 |
| EP | 0547135 | B1 | 6/1993 |
| EP | 0871414 | A0 | 9/1995 |
| EP | 0 592 410 | B1 | 10/1995 |
| EP | 0756498 | A0 | 10/1995 |
| EP | 0 592 410 | B1 | 11/1995 |
| EP | 0786970 | A0 | 5/1996 |
| EP | 0729364 | B1 | 9/1996 |
| EP | 0756498 | B1 | 5/1997 |
| EP | 0778775 | B1 | 6/1997 |
| EP | 0786970 | A0 | 8/1997 |
| EP | 0888142 | A0 | 9/1997 |
| EP | 0971649 | A0 | 10/1998 |
| EP | 0928615 | A1 | 7/1999 |
| EP | 1051204 | A0 | 7/1999 |
| EP | 1089676 | A0 | 12/1999 |
| EP | 0986348 | B1 | 3/2000 |
| EP | 1117446 | A0 | 4/2000 |
| EP | 1 164 976 | A0 | 8/2000 |
| EP | 1158937 | A0 | 9/2000 |
| EP | 1 251 805 | B1 | 10/2000 |
| EP | 1041942 | B1 | 10/2000 |
| EP | 1041943 | B1 | 10/2000 |
| EP | 1171061 | A0 | 10/2000 |
| EP | 1206179 | A0 | 2/2001 |
| EP | 1 233 731 | A0 | 5/2001 |
| EP | 1117446 | B1 | 7/2001 |

(56) References Cited

FOREIGN PATENT DOCUMENTS

| | | | |
|---|---|---|---|
| EP | 1 255 510 | A0 | 8/2001 |
| EP | 1259193 | A0 | 9/2001 |
| EP | 1 233 731 | B1 | 5/2002 |
| EP | 1 330 213 | A0 | 5/2002 |
| EP | 1206179 | B1 | 5/2002 |
| EP | 1347785 | A0 | 8/2002 |
| EP | 1235537 | A0 | 9/2002 |
| EP | 1248655 | A0 | 10/2002 |
| EP | 1251804 | B1 | 10/2002 |
| EP | 1257305 | A0 | 11/2002 |
| EP | 0 971 649 | B1 | 12/2002 |
| EP | 1395208 | A0 | 12/2002 |
| EP | 1 401 359 | A0 | 1/2003 |
| EP | 1406561 | A0 | 1/2003 |
| EP | 1281357 | A2 | 2/2003 |
| EP | 1408882 | A0 | 2/2003 |
| EP | 1 435 878 | A0 | 4/2003 |
| EP | 1 435 879 | A0 | 4/2003 |
| EP | 1 441 672 | A0 | 6/2003 |
| EP | 1 017 868 | B1 | 9/2003 |
| EP | 1354569 | A1 | 10/2003 |
| EP | 1494616 | A0 | 10/2003 |
| EP | 1 519 697 | A0 | 1/2004 |
| EP | 1 539 047 | A0 | 4/2004 |
| EP | 1551274 | A0 | 4/2004 |
| EP | 1 560 542 | A0 | 5/2004 |
| EP | 1414295 | A0 | 5/2004 |
| EP | 1 603 493 | A0 | 9/2004 |
| EP | 1452153 | A1 | 9/2004 |
| EP | 0987998 | B1 | 10/2004 |
| EP | 1 087 727 | B1 | 11/2004 |
| EP | 1499366 | B1 | 1/2005 |
| EP | 1 663 070 | A0 | 3/2005 |
| EP | 1 253 875 | B1 | 4/2005 |
| EP | 1 667 614 | A0 | 4/2005 |
| EP | 1 251 803 | B1 | 6/2005 |
| EP | 1 702 247 | A0 | 7/2005 |
| EP | 1734902 | A0 | 8/2005 |
| EP | 1835948 | A0 | 6/2006 |
| EP | 1863545 | A0 | 9/2006 |
| EP | 1893132 | A0 | 11/2006 |
| EP | 1901681 | A0 | 12/2006 |
| EP | 1 255 510 | B1 | 3/2007 |
| EP | 1835948 | A0 | 9/2007 |
| EP | 1112042 | B1 | 11/2007 |
| EP | 1878407 | A1 | 1/2008 |
| EP | 1886649 | A2 | 2/2008 |
| EP | 1 900 343 | A2 | 3/2008 |
| EP | 1259195 | B1 | 10/2008 |
| EP | 1994913 | | 11/2008 |
| EP | 2 000 115 | A2 | 12/2008 |
| GB | 2440809 | A | 2/2008 |
| JP | 52-086296 | | 7/1977 |
| JP | 62-227352 | | 10/1987 |
| JP | 2002-525169 | | 8/2002 |
| JP | 2002-536115 | | 10/2002 |
| JP | 2003-523262 | | 8/2003 |
| JP | 2003-524504 | | 8/2003 |
| JP | 2005-118585 | | 5/2005 |
| JP | 2007-296375 | | 11/2007 |
| WO | WO-90/09102 | | 8/1990 |
| WO | WO 91/17720 | A | 11/1991 |
| WO | WO-95/24873 | | 9/1995 |
| WO | WO-95/28183 | | 10/1995 |
| WO | WO-96/13227 | | 5/1996 |
| WO | WO-97/32615 | | 9/1997 |
| WO | WO-98/43556 | | 10/1998 |
| WO | WO-98/46165 | | 10/1998 |
| WO | WO-99/37337 | | 7/1999 |
| WO | WO-99/66863 | | 12/1999 |
| WO | WO 00/15148 | | 3/2000 |
| WO | WO 00/18333 | | 4/2000 |
| WO | WO-00/18445 | | 4/2000 |
| WO | WO 00/25702 | A1 | 5/2000 |
| WO | WO 00/047139 | | 8/2000 |
| WO | WO 00/47139 | A1 | 8/2000 |
| WO | WO-00/53125 | | 9/2000 |
| WO | WO-00/62714 | | 10/2000 |
| WO | WO-01/10209 | A1 | 2/2001 |
| WO | WO 01/35870 | A1 | 5/2001 |
| WO | WO-01/41679 | A1 | 6/2001 |
| WO | WO-01/51104 | A1 | 7/2001 |
| WO | WO 01/54625 | A1 | 8/2001 |
| WO | WO-01/58503 | A1 | 8/2001 |
| WO | WO 01/62189 | A1 | 8/2001 |
| WO | WO 01/64137 | A1 | 9/2001 |
| WO | WO 02/36048 | A1 | 5/2002 |
| WO | WO-02/058745 | A1 | 8/2002 |
| WO | WO-02/100301 | A1 | 12/2002 |
| WO | WO-02/102286 | A1 | 12/2002 |
| WO | WO 03/003949 | A2 | 1/2003 |
| WO | WO-03/007795 | A2 | 1/2003 |
| WO | WO-03/009785 | A1 | 2/2003 |
| WO | WO 03/011195 | A2 | 2/2003 |
| WO | WO 03/013239 | | 2/2003 |
| WO | WO 03/028592 | A1 | 4/2003 |
| WO | WO 03/047468 | A1 | 6/2003 |
| WO | WO 00/047139 | | 8/2003 |
| WO | WO-03/079928 | A2 | 10/2003 |
| WO | WO 03/096935 | A1 | 11/2003 |
| WO | WO 2004/004597 | A2 | 1/2004 |
| WO | WO 2004/016200 | A1 | 2/2004 |
| WO | WO 2004/016201 | A2 | 2/2004 |
| WO | WO 2004/019825 | A1 | 3/2004 |
| WO | WO-2004/026117 | A2 | 4/2004 |
| WO | WO 2004/026173 | A2 | 4/2004 |
| WO | WO 2004/043301 | A1 | 5/2004 |
| WO | WO 2004/082527 | A2 | 9/2004 |
| WO | WO 2004/096100 | A1 | 11/2004 |
| WO | WO 2005/021063 | A2 | 3/2005 |
| WO | WO 2005/034812 | A1 | 4/2005 |
| WO | WO 2005/062980 | A | 7/2005 |
| WO | WO 2005/063980 | A | 7/2005 |
| WO | WO-2005/072654 | A1 | 8/2005 |
| WO | WO 2006/066327 | | 6/2006 |
| WO | WO-2006/066327 | A1 | 6/2006 |
| WO | WO 2006/076890 | A1 | 7/2006 |
| WO | WO-2006/102063 | A2 | 9/2006 |
| WO | WO 2006/108090 | A2 | 10/2006 |
| WO | WO 2006/124649 | A2 | 11/2006 |
| WO | WO-2006/124649 | A2 | 11/2006 |
| WO | WO 2006/127756 | A2 | 11/2006 |
| WO | WO 2006/127765 | A1 | 11/2006 |
| WO | WO-2006/132948 | A1 | 12/2006 |
| WO | WO 2007/047488 | A2 | 4/2007 |
| WO | WO 2007/047945 | A2 | 4/2007 |
| WO | WO 2007/059252 | A1 | 5/2007 |
| WO | WO-2007/071436 | A2 | 6/2007 |
| WO | WO 2007/120543 | A1 | 10/2007 |
| WO | WO-2008/028569 | A1 | 3/2008 |
| WO | WO 2008/045949 | | 4/2008 |
| WO | WO 2008/070797 | A2 | 6/2008 |
| WO | WO 2008/079962 | A1 | 7/2008 |
| WO | WO 2008/101083 | A2 | 8/2008 |

OTHER PUBLICATIONS

Translation of Aortenklappenbioprothese erfolgreich in der Entwicklung (2 pages).

Screen shots from http://www.fraunhofer.de/presse/filme/2006/index.jsp (2 pages), 2006.

Liang, Ma, et al., "Double-crowned valved stents for off-pump mitrel valve replacement," European Journal of Cardio-Thoracic Surgery, 194-198 (5 pages), Jun. 13, 2005.

Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.

Translation of DE 19546692 A1 (4 pages).

File history for German Patent DE 195 46 692 filed Dec. 14, 1995 and patented Jul. 11, 2002.

* cited by examiner

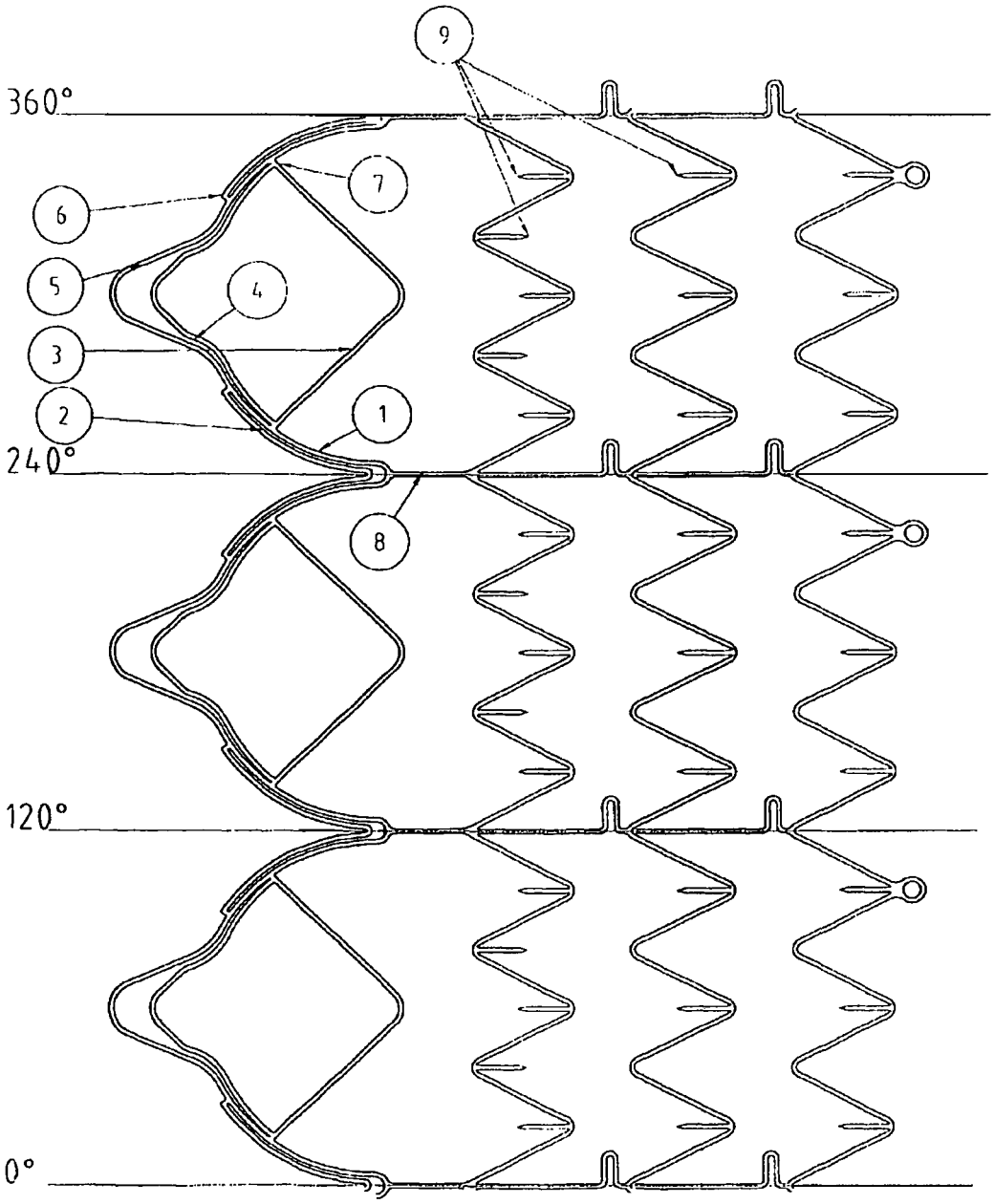
9
360°
7
6
5
4
3
2
1
240°
8
120°
0°

DEVICE FOR FASTENING AND ANCHORING CARDIAC VALVE PROSTHESES

Matter enclosed in heavy brackets [ ] appears in the original patent but forms no part of this reissue specification; matter printed in italics indicates the additions made by reissue.

CROSS-REFERENCE TO RELATED APPLICATIONS

This application is a U.S. national counterpart application of international application serial no. PCT/DE01/00837 filed Feb. 28, 2001, which claims priority to German application serial No. 100 10 074.0 filed Feb. 28, 2000.

BACKGROUND AND SUMMARY OF THE INVENTION

The invention relates to a device for fastening and anchoring cardiac valve prostheses which is essentially formed of wire-shaped interconnected elements. In the folded up state it is allowed to be introduced through the aorta in a minimally invasive manner, and be anchored in the aorta wall after being deployed such that the implanted and secured heart valve prosthesis is allowed to adopt the function of the endogenous heart valve.

Heretofore, it did not succeed in a satisfactory extent to suggest a solution wherein both a secure sealing against the aorta wall and a secure retention can be ensured. On that occasion, such a device or such an anchoring support (stent) must be able to be folded up small enough in order to be stretched then at the site of implantation. With the known solutions a satisfactory enlargement will not be achieved with the appropriate tension force which is allowed to ensure such a retention. Proposals in which a form storage metal (memory metal) is to be used as well do not meet the requirements although an expansion takes place with these materials when a transition temperature has been reached and exceeded, respectively.

The solution as described in U.S. Pat. No. 5,411,552 cannot meet the requirements as well since a relatively instable object is to be used.

Another problem which is solved in an unsatisfactory manner so far is the secure attachment of an artificial or biological heart valve prosthesis. As a rule, the prostheses are lavishly sewn on to a stent. This is time-consuming and has to be carried out with great care in order to avoid damages.

Since the implanted heart valve prostheses have to be able to function over long periods the constructional design plays an essential role as well since damages and leakages can occur after the implantation otherwise which can result in life threatening states of the patient.

Hence, it is an object of the invention to suggest a device for fastening and anchoring heart valve prostheses which can be folded up small enough, and deployed at the site of implantation for a minimally invasive implantation through the aorta wherein a secure retention and a secure sealing with respect to the aorta wall are ensured.

According to the invention this object is solved with a device according to claim 1.

Advantageous embodiments and improvements of the invention can be achieved with the features mentioned in the subclaims.

Three identical pairs of arched elements each are substantial elements of the solution according to the invention which are interconnected in a configuration that is offset by 120°. The two arched elements of one pair are bent opposite to each other in a curved manner and connected by means of solid articulations. The solid articulations simultaneously meet the function of pivot bearings about which the arched elements of one pair can be swivelled similarly as with a seesaw. If a pressure force is exerted upon one of the arched elements, e.g. through the peristaltic action of the aorta, this arched element will be swivelled according to the same direction about the axis of rotation on the solid articulation. Simultaneously, the respective other arched element of the pair will be swivelled opposite thereto. Therefore, one of the two arched elements of the pair is then already pressed against the aorta wall increasing the sealing and the retention.

It is favourable to dimension the arched elements of a pair such that as far as possible the same lever relations are met with respect to the solid articulations forming the pivot bearings, thus rocker arms with an identical length or at least with approximately the same length will be formed.

The relative great distances of the solid articulations predetermined by the configuration of 120° of the pairs of arched elements, and the large surface areas covered by the arched elements as well are also advantageous wherein the distal arched elements do not only serve for fastening the heart valve prosthesis but also adopt a supporting function.

The mentioned advantages can still be improved by means of another curved arched element which is arranged in the distal direction.

On that occasion, the second distal arched element in its distal area is designed in a curved manner approximately like the first distal arched element. Partly, these two arched elements are designed and shaped such that they pass adjacent to each other, and gaps are formed between them. They are allowed to be interconnected at the same place at which the solid articulations are also arranged as a connection toward the arched element curved in the proximal direction. Hence, the formed gaps are open in the distal direction, and portions of the heart valve prosthesis are allowed to be introduced into the gaps and be supported.

At least one portion of a distal arched element is proximally retracted and guided up to a turning point in which adjacent arched elements are collected. With two distally arranged arched elements this applies to the respective distally outer arched element.

For stiffening and as a further possibility of fastening the heart valve prosthesis it is allowed to use an angular curved arched element being proximally retracted as well, the curved portions of which are located between the respective adjacent arched elements and are formed partly following the respective curvature. These arched elements with the distal ends thereof are secured to the one distally outer arched element or the respective distally outer arched element. Herein, the attachment also forms a respective solid articulation. These should still be located in a distance to the other solid articulations connecting one pair.

With a device being implanted and stretched over the pockets of a heart valve prosthesis then can be pushed in, held and supported there.

The construction of the arched element of the device according to the invention supports a heart valve prosthesis in a large-surface manner, and therefore with care. Additionally, it is allowed to be fastened with a substantially lower amount, for example by sewing.

The constructional solution enables a secure retention and the required sealing on the aorta wall, and with respect thereto, respectively. Pressing against the heart valve prosthesis from the inside by means of the arched element is advantageous for the sealing and for a reduced load of the heart valve prosthesis.

The device according to the invention can be implanted by means of a balloon catheter and can be deployed at the site of implatation. Advantageously, for the device is used a form storage metal as well having a suitable transition temperature by means of which an extension can be additionally achieved. For this, an alloy containing nickel and titanium can be employed which is available under the designation of Nitinol.

Moreover, the portion of the device supporting and holding the heart valve prosthesis can be implanted separately to a supporting body which is still referred to hereinafter with the description of an embodiment without reducing the advantageous properties. The implantation of this portion substantially consisting of the three segments having the heart valve prosthesis attached thereto then can operatively take place in a conventional form.

In the text that follows, the invention will be explained in more detail according to an embodiment in which

BRIEF DESCRIPTION OF THE DRAWINGS

FIG. 1 shows a developed view of an embodiment of a device according to the invention.

DETAILED DESCRIPTION OF THE DRAWINGS

In FIG. 1 is shown a developed view of an embodiment of a device according to the invention. The device is radially symmetrically designed wherein three identical portions are used in a configuration of 120°.

Each portion uses an arched element construction as a carrier and for fastening an artificial or biological heart valve prosthesis.

With this embodiment two arched elements 4 and 5 are used which are distally arranged outside wherein the outer arched element 5 could be abandoned as the case may be.

The arched element 4 bent into a curved manner is connected to an arched element 3 which is bent in the opposite direction. The two sided connections represent solid articulations 7 which simultaneously adopt pivot functions for the two arched elements 3 and 4 representing levers as it is already described in the general part of the description.

The second arched element 3 which is outwardly bent and distally arranged increases the stability and offers an additional supporting and fastening possibility for the heart valve prosthesis. On that occasion, the two distally outer arched elements 4 and 5 are interconnected as well, wherein this connection is allowed to occur at the same place at which the solid articulations 7 are also arranged.

There are gaps between the two arched elements 4 and 5 which are open from the distal direction into which the portions of the heart valve prosthesis can be introduced and fixed there.

The arched element 5 being the outer one here is further inwardly pulled in the proximal direction, and is connected with its end to a respective supporting ridge 8. In this embodiment, the supporting ridges 8 are aligned in parallel to the longitudinal axis of the device, and together with saw tooth shaped, rhombic or meander shaped transversal ridges they form a supporting body which in the deployed state closely fits on the aorta wall. For interlocking, additional tips 9 can be present and designed, respectively, on the supporting ridges 8, and/or the transversal ridges which interlock in the aorta wall.

The configuration and length of the supporting ridges 8, and the respective great distance toward the heart valve prosthesis fastened in the area of the arched elements 3, 4 and 5 enable positioning the heart valve prosthesis without locking and covering the coronary vessels, respectively.

With the embodiment as shown herein, additional arched elements 2 being proximally pulled in are present between the individual segments used in a configuration of 120° which are connected to the distally outer arched elements 5. Herein, the connections are solid articulations 6 as well, however, which should be arranged in a distance toward the solid articulations 7 as far as possible. Thus, two levers per segment can be used, and forces twice as large can be realized with such a double-reflected structure in order to fix the device.

In the deployed implanted state the portions of the heart valve prosthesis can be mutually introduced in turn between the portions 1 of the arched elements 5 and the arched elements 2, thus being supported and fixed thereto.

The number of the arched elements used can still be increased, however, to improve the retention and to further decrease the load of the heart valve prosthesis.

The invention claimed is:

1. A device for fastening and anchoring a heart valve prosthesis, the device consisting of three identical sections, each section being coupled to adjacent sections on each side of said section by an elongated supporting ridge extending in a direction generally parallel to a longitudinal axis of the device, each section having a first arched element arched in a first direction, a second arched element arched in the first direction, and a third arched element arched in a second direction opposite from the first direction, the second and third arched elements being coupled to the first arched element at first points to define between the first and second arched elements a first space, each section further comprising a fourth arched element arched in the second direction and having ends coupled to the first arched element of said section and [a] *the* first arched element of an adjacent section at second points distinct from the first points to define between the fourth arched element and the adjacent first arched elements a second space.

2. A device for supporting a heart valve prosthesis, the device consisting essentially of three substantially identical elements, each element being coupled to adjacent elements on each side of said element by an elongated supporting member extending in a direction generally parallel to a longitudinal axis of the device, each element including a first arched member coupled to, and extending in a first direction generally away from said first arched member's respective supporting members, and a second arched member coupled to the first arched member at points different from the first arched member's coupling to its respective supporting members, the second arched member extending generally in a second direction opposite from the first direction, wherein each element further includes a third arched member coupled to the first arched member at substantially the same points as the second arched member is coupled to the first arched member, the third arched member extending generally in the first direction, each element further including a pair of fourth arched members, each of said fourth arched members extending alongside, and conforming generally to, the curvature of a portion of the first arched member, each of the fourth arched members being coupled to a first arched member intermediate opposite ends of said first arched member and extending from said coupling to said first arched member generally in said second direction toward a respective supporting member.

3. The device of claim 2 wherein each fourth arched member extends to a point adjacent a respective supporting member, turns, and extends generally in the first direction, conforming generally to the curvature of a portion of a first arched member of an adjacent element on one side of said element.

4. The device of claim 3 wherein each element further includes transversal members extending between its respective supporting members.

5. The device of claim 4 wherein at least some of said transversal members include tips to facilitate anchoring of said device into tissue of a vessel or the heart of a wearer of the device.

6. The device of claim 4 constructed from memory metal.

7. The device of claim 3 constructed from memory metal.

8. The device of claim 2 wherein each element further includes transversal members extending between its respective supporting members.

9. The device of claim 8 wherein at least some of said transversal members include tips to facilitate anchoring of said device into tissue of a vessel or the heart of a wearer of the device.

10. The device of claim 8 constructed from memory metal.

11. The device of claim 2 constructed from memory metal.

*12. A medical device, in combination with a heart valve prosthesis, the medical device consisting of three substantially identical sections, each section being coupled to adjacent sections on each side of the section, the medical device being implantable in a body via a catheter and including a collapsed mode and an expanded mode, each section including:*

*a first arched element arched in a first direction, the first arched element disposed at a distal end of the device;*

*a second arched element arched in the first direction, the second arched element disposed at the distal end of the device and connected to the first arched element at first points; and*

*a fourth arched element arched in a second direction opposite from the first direction and having ends coupled to the first arched element of said section and the first arched element of an adjacent section at second points distinct from the first points to define between the fourth arched element and the adjacent first arched elements a space;*

*wherein the heart valve prosthesis is fixedly attached to the first, second, and fourth arched elements of each of the three sections and remains fixedly attached to function as a heart valve after removal of the catheter from the body, the heart valve prosthesis repeatedly opening and closing to allow and prevent blood flow, respectively, through the medical device.*

*13. The medical device, in combination with the heart valve prosthesis of claim 12, each section further including:*

*a third arched element arched in the second direction, the third arched element connected to the first and second arched elements at the first points.*

*14. The medical device, in combination with the heart valve prosthesis of claim 13, wherein each section further includes an eyelet element disposed at a proximal end of the device opposite the distal end.*

*15. The medical device, in combination with the heart valve prosthesis of claim 12, wherein each of the three fourth arched elements conforms generally to a curvature of a portion of the first arched element of the first section and the curvature of a portion of the first arched element of the adjacent section.*

*16. The medical device, in combination with the heart valve prosthesis of claim 12, wherein at least one of the second points pivots when a pressure force is exerted upon one of the first or fourth arched elements.*

*17. The medical device, in combination with the heart valve prosthesis of claim 12, wherein the device is configured to be implanted within an aorta.*

*18. The medical device, in combination with the heart valve prosthesis of claim 12, wherein each section is coupled to the adjacent sections by a supporting ridge, each section further including transversal members extending between adjacent elongated supporting ridges.*

*19. The medical device, in combination with the heart valve prosthesis of claim 18, wherein at least some of said transversal members include tips to facilitate anchoring of said device into tissue of a vessel or a heart of a patient.*

*20. The medical device, in combination with the heart valve prosthesis of claim 18, wherein the transversal members have a saw-tooth shape.*

*21. The medical device, in combination with the heart valve prosthesis of claim 18, wherein the transversal members have a rhombic shape.*

*22. The medical device, in combination with the heart valve prosthesis of claim 12, wherein the heart valve prosthesis is a biological heart valve prosthesis.*

*23. The medical device, in combination with the heart valve prosthesis of claim 12, wherein the heart valve prosthesis is an artificial heart valve prosthesis.*

*24. The medical device, in combination with the heart valve prosthesis of claim 12, wherein the three sections are spaced substantially 120 degrees apart.*

*25. The medical device, in combination with the heart valve prosthesis of claim 12, wherein the device is constructed from memory metal.*

*26. The medical device, in combination with the heart valve prosthesis of claim 12, wherein the device is balloon expandable.*

*27. A medical device, in combination with a heart valve prosthesis, the medical device consisting of three substantially identical sections, each section being coupled to adjacent sections on each side of the section, the medical device being implantable in a body via a catheter and having a first, compressed mode and a second, expanded mode, each section including:*

*a first arched element arched in a first direction, the first arched element disposed at a distal end of the device;*

*a third arched element arched in a second direction opposite from the first direction, the first and third arched elements connected to each other at a first point, wherein between an apex of the first arched element and an apex of the third arched element there is a space; and*

*a fourth arched element arched in a direction opposite from the first direction and having a first end coupled to the first arched element of said section at a second point and a second end coupled to the first arched element of an adjacent section at a third point, the second point and the third point being distinct from the first point to define between the fourth arched element and the adjacent first arched elements a space;*

*wherein the heart valve prosthesis is fixedly attached to the first and fourth arched elements of each of the three sections and remains fixedly attached to function as a heart valve after removal of the catheter from the body, the heart valve prosthesis repeatedly opening and closing to allow and prevent blood flow, respectively, through the medical device.*

*28. The medical device, in combination with the heart valve prosthesis of claim 27, wherein the first point is a pivot point about which the third arched element can move.*

*29. A medical device, in combination with a heart valve prosthesis fixedly attached to the medical device, the medical*

*device consisting of three substantially identical sections, each section being coupled to adjacent sections on each side of the section, the medical device being implantable in a body via a catheter and having a first, compressed mode and a second, expanded mode, each section including:*

*a first arched element arched in a first direction, the first arched element connected to a supporting ridge and disposed on a first, distal end of the supporting ridge;*

*a third arched element arched in a second direction opposite from the first direction, the first and third arched elements connected to each other at a first point, wherein between an apex of the first arched element and an apex of the third arched element there is a space; and*

*a fourth arched element arched in a direction opposite from the first direction and having ends coupled to the first arched element of said section and the first arched element of an adjacent section, wherein a curvature of the fourth arched element is different from a curvature of the third arched element; and*

*a plurality of undulating transverse ridges connected to the supporting ridge and disposed on a second, proximal end of the supporting ridge opposite the first, distal end, such that the supporting ridge is disposed proximal to the first arched element and distal to the plurality of undulating transverse ridges, the plurality of undulating transverse ridges including at least two sets of undulating transverse ridges, each set of undulating transverse ridges extending around a circumference of the medical device;*

*wherein the heart valve prosthesis remains fixedly attached to the medical device to function as a heart valve after removal of the catheter from the body, the heart valve prosthesis repeatedly opening and closing to allow and prevent blood flow, respectively, through the medical device.*

*30. The medical device, in combination with a heart valve prosthesis of claim 29, further including an eyelet element connected to at least one of the plurality of undulating transverse ridges.*

*31. The medical device, in combination with a heart valve prosthesis of claim 29, wherein the plurality of undulating transverse ridges form a supporting body configured to engage a portion of a vessel wall when the medical device is in the expanded mode at a deployed state.*

*32. The medical device, in combination with a heart valve prosthesis of claim 29, wherein the device is configured to be implanted within an aorta.*

*33. The medical device, in combination with a heart valve prosthesis of claim 29, wherein at least one of the plurality of undulating transverse ridges includes tips to facilitate anchoring of the device into tissue of a vessel or a heart of a patient.*

*34. The medical device, in combination with a heart valve prosthesis of claim 29, wherein the plurality of undulating transverse ridges have a saw-tooth shape.*

*35. The medical device, in combination with a heart valve prosthesis of claim 29, wherein the plurality of undulating transverse ridges have a rhombic shape.*

*36. The medical device, in combination with a heart valve prosthesis of claim 29, wherein the heart valve prosthesis is a biological heart valve prosthesis.*

*37. The medical device, in combination with a heart valve prosthesis of claim 29, wherein the heart valve prosthesis is an artificial heart valve prosthesis.*

*38. The medical device, in combination with a heart valve prosthesis of claim 29, wherein the three sections are spaced substantially 120 degrees apart.*

*39. The medical device, in combination with a heart valve prosthesis of claim 29, wherein the device is constructed from memory metal.*

*40. The medical device, in combination with a heart valve prosthesis of claim 29, wherein the device is balloon expandable.*

* * * * *